(12) United States Patent
Friesner et al.

(10) Patent No.: US 8,510,058 B2
(45) Date of Patent: Aug. 13, 2013

(54) BINDING AFFINITY SCORING FUNCTION PENALIZING COMPOUNDS WHICH MAKE UNFAVORABLE HYDROPHOBIC CONTACTS WITH LOCALIZED WATER MOLECULES IN THE RECEPTOR ACTIVE SITE

(75) Inventors: Richard A. Friesner, New York, NY (US); Robert Murphy, Jamul, CA (US)

(73) Assignee: Schrodinger, LLC, New York, NY (US)

( * ) Notice: Subject to any disclaimer, the term of this patent is extended or adjusted under 35 U.S.C. 154(b) by 0 days.

(21) Appl. No.: 13/079,725

(22) Filed: Apr. 4, 2011

(65) Prior Publication Data

US 2012/0252683 A1    Oct. 4, 2012

(51) Int. Cl.
*G06F 17/11* (2006.01)
*G06F 17/50* (2006.01)
*G06F 19/00* (2006.01)

(52) U.S. Cl.
USPC .............................................. 702/19; 703/11

(58) Field of Classification Search
None
See application file for complete search history.

(56) References Cited

U.S. PATENT DOCUMENTS

| | | |
|---|---|---|
| 7,739,091 B2 | 6/2010 | Audie |
| 7,756,674 B2 | 7/2010 | Young et al. |
| 2005/0027458 A1 | 2/2005 | Merz et al. |
| 2006/0041414 A1 | 2/2006 | Ho |
| 2007/0006118 A1 | 1/2007 | Pierrat et al. |
| 2007/0061118 A1 | 3/2007 | Friesner et al. |
| 2010/0241412 A1 | 9/2010 | Young et al. |

FOREIGN PATENT DOCUMENTS

WO    2008/141260    11/2008

OTHER PUBLICATIONS

Mancera et al. Chemical Physics Letters, 399, 271-275, 2004.*
Verdonk et al. J. Med. Chem., 2005, 48 (20), p. 6504-6515.*
Friesner et al., "Extra Precision Glide; Docking and Scoring Incorporating a Model of Hydrophobic Enclosure for Protein-Ligand Complexes," J. Med. Chem. Sep. 2006, 49, 6177-6196.
Li et al., "Thermodynamics of Buried Water Clusters at a Protein-Ligand Binding Interface," J. Phys. Chem. B 2006, 110, 1464-1475, Dec. 2005.
Schnecke et al., "Virtual screening with solvation and ligand-induced complementarity," Perspectives in Drug Discovery and Design, 20:171-190, Dec. 2000, pp. 171, 172, 174, 178, 181, 187.

* cited by examiner

*Primary Examiner* — Michael Borin
(74) *Attorney, Agent, or Firm* — Fish & Richardson P.C.

(57) ABSTRACT

A method of scoring binding affinity of a proposed ligand molecule for a receptor molecule using a computer and computer data bases, which accounts for the increase in energy required where docking disrupts water molecules that are localized at ligand hydration sites. The method uses computer-stored data representing a predicted ligand-receptor structure (preferably one that is validated). The computerized scoring analysis includes determining whether the receptor includes one or more hydration sites occupied by localized water, and, if so, assessing a penalty if docking the ligand into the receptor results in unfavorable interaction of the ligand with a localized water molecule remaining at the receptor hydration site (i.e. after docking).

16 Claims, 4 Drawing Sheets

(4 of 4 Drawing Sheet(s) Filed in Color)

BINDING AFFINITY SCORING FUNCTION PENALIZING COMPOUNDS WHICH MAKE UNFAVORABLE HYDROPHOBIC CONTACTS WITH LOCALIZED WATER MOLECULES IN THE RECEPTOR ACTIVE SITE

TECHNICAL FIELD

The invention is in the general field of computer-based methods for estimating binding affinity between a ligand and a receptor molecule.

RELATED CASES

Simultaneously with the filing of this patent application we are filing a commonly owned U.S. patent application entitled "Scoring Function Penalizing Compounds Which Desolvate Charged Protein Side Chains Structure", which application is hereby incorporated by reference in its entirety.

BACKGROUND

Many drugs operate by chemically binding to specific molecular receptors. Molecular receptors typically are specific proteins (a term that includes glycoproteins and lipoproteins) in an animal such as a human being, and drug design and selection can be facilitated by accurately estimating the binding affinity of a drug to a protein, or, more generally, estimating the binding affinity of a ligand to a receptor, the term receptor being used to mean any moiety that specifically binds the ligand.

One way to determine receptor-ligand binding affinity uses the molecular structure that results when the ligand binds to the receptor ("the ligand-receptor complex"). Such structures may be studied by x-ray crystallography. The publicly accessible protein data bank (PDB) now contains more than 70,000 x-ray crystal structures, and pharmaceutical and biotechnology companies have an order of magnitude more proprietary structures. Many of these structures have been co-crystallized with small molecules bound to them. The examination of such structures, and deployment of the knowledge thereby gained to design new, more potent, and more specific inhibitors, is referred to as structure-based drug design.

Computational modeling facilitates structure-based drug design. One aspect of modeling detailed below involves scoring functions that use simulation techniques, such as molecular dynamics, Monte Carlo, or continuum electrostatics calculations. Scoring functions can be problematic when one is required to calculate a very small difference (the binding affinity) between two very large numbers (the free energies of the complex and of the separated protein and ligand). An alternative approach is to develop an empirical scoring function, based on the geometry of the complex, which directly evaluates the desired quantity. Such an approach has the advantage of being extremely fast as well as being amenable to fitting to experimental data, large amounts of which are now publicly available. Commonly owned US 2007/0061118 A1 (hereby incorporated by reference), which is hereby incorporated by reference in its entirety, discloses such scoring functions.

It is desirable to increase the accuracy and robustness of scoring functions by making material improvements in the functional form that better reflect physical reality. Commonly owned PCT application WO/2008/141260 (hereby incorporated by reference) describes improvements intended to improve rank ordering of the binding affinities of a series of ligands bound to a specified receptor.

A second major problem with scoring functions is that they may assign better (more negative) binding affinity scores to inactive compounds (i.e. compounds that would not be determined to bind to the receptor in a typical experimental screening protocol) than to active compounds. If a large number of inactive compounds are ranked ahead of active compounds, a principal function of docking, which is to discover new active compounds against a specified receptor from a very large compound library (often millions of compounds), becomes difficult to carry out effectively. Therefore, substantially reducing the number of "false positives" (ranking of inactive compounds as active) would greatly improve scoring function performance.

SUMMARY

We have discovered a method of scoring binding affinity of a proposed ligand molecule for a receptor molecule using a computer and computer data bases, which accounts for the increase in energy required where docking disrupts water molecules that are localized at ligand hydration sites. The method uses computer-stored data representing a predicted ligand-receptor structure (preferably one that is validated). The computerized scoring analysis includes determining whether the receptor includes one or more hydration sites occupied by localized water, and, if so, assessing a penalty if docking the ligand into the receptor results in unfavorable interaction of the ligand with a localized water molecule remaining at the receptor hydration site (i.e. after docking) Penalty assessment for a given case is performed via an empirical analysis, where the specific penalties assigned to particular set of interactions of the ligand with localized water molecules remaining at the receptor hydration sites are effectively precomputed and reapplied. Further, such a penalty assessment requires only a single configuration of the receptor-ligand complex, and is significantly faster (<½ hour) than alternative pure physics-based approaches attempt to fully describe the whole range of physics manifest by the ligand-receptor complex ensemble.

We include in the term "localized water" waters that are localized or quasi-localized, i.e., any water occupying a hydration site where the local water occupancy density at the hydration site is substantially higher than the number density of bulk fluid. The presence of such localized water at hydration sites can be determined by running and analyzing a molecular dynamics trajectory, or from experimental data such as water densities obtained from x-ray crystallographic experiments. In contrast to such localized water-based penalties, interactions with water molecules residing in regions of bulk density are not assigned a significant penalty. For example in preferred embodiments a penalty is applied to the binding affinity score of the ligand only if the free energy of displacement of a water molecule from the receptor site into bulk waters is determined to be more favorable than a specified cutoff value (e.g., 0 kcal/mole) of the energy gained by displacing the water from the receptor site into the bulk water. Note, other reference states for determining the free energy (and thus also the particular value of the cutoff) of the water in the hydration sites might be used to classify the water in the hydration sites. For example, transfer of the water from the hydration site to the gas phase might be used, where the specific cutoff employed would then be varied to implicitly include the transfer of the water from the gas phase to the liquid phase. In that case the cutoff value would be adjusted to reflect this variation. Other such possible reference states might include use of displacement of the water from the hydration site to the crystalline phase, or displacement water from the hydration site to any other thermodynamically well-defined environment. Alternatively, the energetic favorability of the water molecule in the localized site is estimated from features of the site such as the hydrophobicity of the site, specific interactions with receptor groups, using various types of calculations, including but not limited to molecular dynamics simulations, Monte Carlo simulations, exhaustive enumeration of geometries of the water molecule within the site, and optimization (via for example energy minimization) of the position of the water molecule within the site. Localized water sites may be identified by active-site solvation analysis such as the WaterMap analysis for assigning displacement free energies described below.

In preferred embodiments, the receptor hydration sites are determined by computerized sampling of sites for hydration followed by computerized assignment of water occupancies for the various sampled sites. This includes the special case where the occupancies were discretely assigned to be 0 or 1. A penalty is assessed for compounds when the localized water within a hydration site interacts with a hydrophobic ligand atom or when the localized water within a hydration site interacts with a hydrophobic ligand atom, e.g., at a distance of 5 Å or less. No penalty is assessed for interaction with a hydrophobic ligand atom having a positive ligand atom 4 atoms or closer to it (based on bond connectivity of the atoms in the ligand). No penalty is assessed: a) when the hydrophobic ligand atom is Cl or Br; b) when the hydrophobic ligand atom is not part of a ligand —$CH_3$ group or a ligand atom within 3 atoms of a —$CH_3$ group, and if the localized water within a hydration site has access to surrounding water because it borders the edge of a hydrophobic pocket; c) when the localized water within a hydration site is within 5 Å of a positively charged ligand atom regardless of any other interactions; d) when the localized water within a hydration site has hydrogen bonds to the ligand, regardless of any other interactions. Preferably, receptor sites with a localized water are determined to be waters that are predicted to have an occupancy in the reference frame of the protein significantly (e.g., 1.5×) above the bulk water occupancy. No penalty is assessed if the localized water within a hydration site has hydrogen bonds to the ligand, regardless of any other interactions. Hydrogen bond here is taken to include C—H—O interactions when the C—H is an aromatic C—H group, with suitable geometries, as discussed in this application below, as well as more traditional hydrogen bonds. Scoring can include estimating the energetic favorability of the water molecule in the hydration site from the hydrophobicity of the site or from specific interactions with receptor groups. Estimating energetic favorability can include calculation such as molecular dynamics simulations, Monte Carlo simulations, exhaustive enumeration of geometries of the water molecule within the site, and optimization (via for example energy minimization) of the position of the water molecule within the site. Free energies of displacement of a water molecule from the receptor site into bulk water may be determined by molecular dynamics simulation followed by the application of modified inhomogeneous solvation to assign displacement free energies.

Other features and advantages of the invention are apparent from the following description, and from the claims.

DESCRIPTION OF DRAWINGS

The file of this patent contains at least one drawing executed in color. Copies of this patent with color drawings will be provided by the Patent and Trademark Office upon request and payment of the necessary fee.

DETAILED DESCRIPTION

Figure 1:
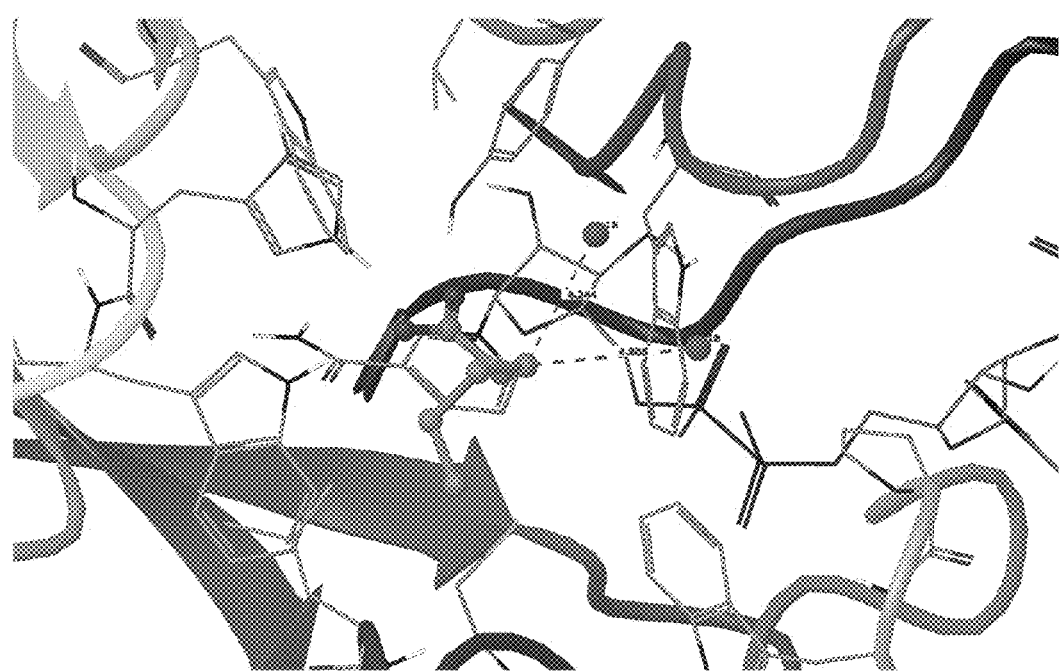
FIG. 1. Active ligand 2iq0 is here depicted to be forming unfavorable contacts with water molecules 16 and 18. This ligand suffers a computed 1.0 kcal/mol penalty bringing its estimated binding affinity in closer agreement with the experimentally measured value.

Practicing the invention begins with a receptor (or "target", typically a protein) structure that has sufficient resolution to permit the use of computational software to "dock" a small molecule ligand into the correct position and orient it in the receptor active site cavity and to calculate a binding affinity of the ligand given this structure. Computer software programs that perform this task are referred to as "docking" programs.

A docking program typically carries out two distinct tasks to model receptor-ligand binding. First, a structure of a receptor-ligand complex is predicted by docking the ligand into the receptor structure. When this protocol fails to produce an accurate structure of the protein-ligand complex, use of a different structure of the receptor as a starting point is required. The problem of constructing alternative receptor structures that are modified to accept ligands requiring a substantial change in receptor conformation ("induced fit") is a very important one.

Various adequate receptor-ligand structure prediction programs are well known and can be used for the starting point, and those in the art will understand that no particular methodology is critical. Examples of such functions that are readily available include: Glide, GOLD, FRED, FlexX, or AutoDock, among many others. Once in possession of a receptor structure in reasonable agreement with experimental data, the second task of the docking program is to calculate a receptor-ligand binding affinity, given as an input the docked structure. A mathematical function employed to calculate the binding affinity (or a contribution thereto) is referred to as a "scoring function." Improvements to such scoring functions for calculating receptor-ligand binding affinity are the subject of this invention.

The estimates of receptor-ligand binding affinities described below are applicable when a structure of the receptor-ligand complex is represented by a suitable structural model. There are a number of ways to characterize the quality of structural models of receptor-ligand complexes, so long as the model adequately agrees with experimental data. Measures of structural agreement such as RMSD, DME, or SIFt score among others might be used. Accurate scores are typically but not exclusively obtained using: i) a small root mean square deviation (RMSD) from the experimental structure (typically less than 2 Angstroms, although the required value will vary depending upon details of the complex), ii) recognition of the formation of substantially all hydrogen bonds seen in the experimental complex, iii) appropriate placement of substantially all hydrophobic groups in the correct receptor cavities, and iv) the absence of incorrect structural or electrostatic clashes that could lead to the assignment of substantially incorrect penalty terms. Since relative binding affinity of ligands to a given receptor is under consideration, a constant offset, as is in many cases engendered by reorganization energy of the receptor active site to accommodate the ligand, has no effect on practical applications.

In many (although not all) cases, the receptor can adopt more than one fundamentally different conformation in response to a class of ligands (e.g., DFG-in and DFG-out binders to p38 map kinase); to compare the binding free energies in such cases, different core reorganization parameters may be required for the different receptor conformations. Where calculation of these parameters is not practical from first principles they are treated as adjustable, receptor specific parameters. Other parameters are however contained in a global model which is not receptor-specific or even specific to a particular class of receptors.

The present invention is focused on improving the ability of the scoring function to discriminate inactive and active compounds against a given receptor. While active compounds for a wide range of receptors are readily found in the Protein Data Bank (PDB), our data below validating the invention required also assessed known inactive compounds or an approximate, but sufficiently accurate, model for a library of such compounds. Accessing known inactive compounds from publicly available data is challenging. Therefore, we have devised an alternative protocol, to represent an approximate but sufficiently accurate model of a library of inactive compounds, which is based on the use of a random library of 1000 drug-like compounds. These compounds are docked into a conformation of the receptor, and predicted binding affinities are obtained for each compound using various proposed improvements to the scoring function.

Our scoring function is calibrated so that active compounds achieve scores that are typically close to experimental binding affinities, with a standard deviation of approximately 1 log unit of binding affinity (~1.5 kcal/mole). An experimental "hit" in a random screen in the pharmaceutical industry is generally taken to have a binding affinity of ~7.0 kcal/mole or more (~10 µm concentration). Given the intrinsic fluctuations in the scoring function of 1.5-2.0 kcal/mole, we set the computational threshold for estimating hits at a score of −9.0 kcal/mole; thus any compound in the random 1000 compound library which scores −9.0 or less is predicted to be a hit. Other compounds in the −7.0 to −9.0 range are predicted as possible hits as well, but such scores may also be due to the noise in the scoring function which we are unable at present to reduce further (in part due to limitations on the publicly available experimental data). Hence, we focus in developing our improvements on ensuring that the number of random compounds scoring more negatively than −9.0 is compatible with experimental hit rates for random drug-like compound libraries The hit rate for experimental screens will vary depending upon the receptor, but an illustrative "average" hit rate is 0.5%, or 5 compounds out of 1000. Thus, if substantially more than 5 compounds achieve a score of −9.0 kcal/mole, the assumption is made that inactive compounds are receiving scores that are too favorable. In general, reduction of the number of random library compounds scoring more negatively than −9.0 is taken as improvement of the scoring function, as in the absence of fluctuations, one would expect even fewer (0-2) compounds in this range.

In such a situation, the scoring function may be improved by adding positive "penalty" terms which reduce the magnitude of the predicted binding affinity. Such terms represent physical processes which make binding less favorable. An example of a process of this type would be a desolvation in which a polar group of the protein or ligand is blocked by nonpolar groups of the ligand and loses access to water. This results in a large loss in free energy, making the compound inactive. If the loss of free energy is sufficiently large, then such penalties will only rarely (if at all) be observed in complexes with active compounds. This means that the new terms must be derived by examining the structures produced when the random library is docked into the receptor.

The invention described in this application utilizes a description of localized (as described above) water structure in the receptor active site. One but by no means the only way to do so is to use technology designated "WaterMap" (U.S. Pat. No. 7,756,674, hereby incorporated by reference). WaterMap uses molecular dynamics simulations to place waters at various locations in the active site, and assigns estimated enthalpies and entropies that would be obtained if the water were displaced to bulk solvent by the ligand. The enthalpies and entropies are estimated via a modified version of inhomogeneous solvation theory. Other techniques could be used to place localized waters and estimate their entropies and enthalpies. The invention can be applied as long as the locations of localized waters are specified. The displacement free energies may lead to better accuracy, but significant benefit of the invention can be obtained as long as localized water positions can be enumerated. Such positions can be derived not only from computational methods but also from experimental data, such as x-ray crystallography. Crystallography determines some localized water positions, but not others (typically depending upon the degree of localization). This invention is intended to apply regardless of how the localized water distribution is determined. Other ways to establish the existence of localized water include: appropriate analysis of explicitly solvated Monte Carlo simulations, applications of RISM-type theories, or NMR experiments among other techniques.

The novel component of the invention is the development of a specific mathematical algorithm which detects under what conditions a penalty term should be applied. We have developed this algorithm based on a combination of the basic physical chemistry principles, outlined above, and empirical optimization in which we have designed the algorithm to avoid inappropriately penalizing (i.e. applying a penalty that would make the score of the compound agree less well with experimental binding affinity data than if the penalty were not applied) known complexes of active compounds, taken from the protein data bank (PDB), while at the same time maximizing the number of favorably scoring random data base compounds that are penalized. Details of the optimization protocol are outlined below, after a description of the algorithm itself.

The following detailed description of the invention is used to evaluate assignment of a penalty term to each unstable water generated by a WaterMap calculation in the receptor active site in the absence of any ligand. An "unstable" WaterMap water is defined in our current best practice to be a localized water within a hydration site (or a "water cluster") with an estimated free energy greater (more positive, hence more unstable in the protein active site than it would be in the bulk fluid) than 1.0 kcal/mole. Other cutoffs and definitions of what constitutes an unstable water could be used.

The basic physical idea of the invention is that an unstable WaterMap water cluster will be rendered even more unstable if that water makes hydrophobic contact with one or more ligand atoms. Standard definitions of what constitutes a hydrophobic atom are used in our current best practice (see appendix I); other definitions could be used as well. A water molecule cannot form hydrogen bonds with a hydrophobic ligand atom. A water in bulk solution will typically be able to alter its distribution of geometries so at to evade the hydrophobic atom(s) of the ligand and make hydrogen bonds with other bulk waters, at some cost in entropy. However, a water found to be unstable by a WaterMap calculation is by definition localized to some degree in a confined active site, and is already being forced to evade features of the protein (which is what is causing it to be unstable). Hence, contacts of this water with hydrophobic ligand atoms will cause a greater unfavorable increase in free energy than a similar contact would in bulk solution, and this differential is what is being approximately modeled by adding a penalty term to the binding affinity.

The amount of the penalty for any given water molecule will depend upon a number of factors; the specific distance of the hydrophobic ligand atom (beyond some distance, there is no effective contact, and no penalty is applied), the number of contacts, whether the ligand makes a hydrogen bond to the water as well as a hydrophobic contact (in which case the water has compensated effectively for the hydrophobic contact and no penalty needs to be applied), and other factors detailed below. Another important question is what counts as a hydrogen bond. An empirical survey of ligand-water structure in active complexes conclusively indicates that a C—H—O hydrogen bond, should not receive a penalty, however, such an interaction is not sufficient to turn off the penalty if there are other unfavorable hydrophobic contacts. Finally, in addition to a potential penalty term for each unstable WaterMap water, we define an overall penalty term for the ligand which is based on assessing water-ligand contacts for the entire ligand. The idea behind this term is that as the total number of contacts increase, the perturbation of the overall water structure in the active site increases as well, and a threshold is reached where there are unfavorable consequences that go beyond individual waters. The specifics of this term are described below, and again have been developed by testing the term against the entire set of PDB complexes with active ligands.

The specifics of the invention are as follows:

1) for each WaterMap water calculate the number of contacts of this water with hydrophobic ligand atoms within 5 angstroms of the water atom.
   skip ligand atoms which are
   a) within 1-4 distance of a positive ligand atom
   b) Cl or Br
   c) ligand Ch3 groups and ligand atoms within a 1-3 distance of a ch3 group if the
   WaterMap water is on the edge of the pocket near solution. The solvation of the water is determined using the water packing algorithm of glide (not WaterMap).
   d) If the water has 1 ligand contact using the above rules and this water is within 5 A of a positively charged ligand atom, set the ligand contact to zero (negate the 1 contact).

2) for each WaterMap water calculate the number of contacts of this water with phobic protein atoms within 5 angstroms of the water.
   a) calculate the number of contacts the water makes with polar (O of C=O or N of NH) protein atoms that are not hydrogen bound to the protein and are oriented toward the water. The orientation must be such that the angle made by the C=O-water or NH-water triplet is greater than 108 degrees.

3) for each WaterMap water calculate a fractional number representing the extent to which the water is displaced by contacts with ligand heavy (non-hydrogen) atoms. The displacement fraction is calculated as follows;
   a) for each ligand atom i calculate the distance d to the WaterMap water.
   b) calculate the sum r the ligand Vdw radius r_i and a fixed water Vdw radius of 2.2 A, r=R_i+2.2.
   c) If d<r then the contribution vac_i that ligand atom i makes to the evacuation of water i is $vac\_i=1.0-d/r\ r<=d,\ vac\_i=0.0\ r>d.$ the total fraction that water i is removed is the sum over such v_i with the sum limited a maximum of 1.0.

4) calculate the number of hydrogen bonds each WaterMap water makes with the ligand. Ligand atoms H bonded to waters are donors and acceptor atoms in addition to ligand F, Cl, Br, I atoms. The water ligand atom distance (d) must satisfy;
   a) atoms other than Cl d<=3.8 A.
   c) Cl atoms d<=5.2 A.
   For ligand donor atoms or acceptors with one connection (X—H) the X—H to water angle must be greater than 130.0 degrees for non-halogen atoms and 100 degrees for halogen atoms. For ligand acceptor atoms with two connections the two vectors formed by the two atoms connected to the acceptor are summed and the angle between this sum vector and the vector connecting the acceptor and the water molecule must be greater than 65 degrees.

5) Assign a penalty to each WaterMap water that meets the following criteria;
   a) has 1 or more ligand contacts.
   b) is unstable by 1 kcal/mole or more.
   c) has no hydrogen bonds to the ligand.
   d) has a displacement fraction (see 3) less than 60%.
   e) does NOT satisfy any of the following conditions
   e1) if the water has 3 or fewer ligand contacts and said water has 2 or more contacts (within 4.5 A) with neighboring waters that satisfy the following;
   e1a) neighbor must be unstable by 0.5 kcal or more (check this, could be stable)
   e1b) neighbor must be less than 10% evacuated by ligand contacts.
   e1c) neighbor has 2 or fewer ligand contacts and less than 5 protein contacts
   e1d) neighbor has less than 4 hydrogen bonds to the ligand.
   e2) if water has 3 or fewer ligand contacts and said water is within 5 A of a ligand ring atom which contains a positive charge in the ring.
   e3) if water has 1 or more contacts less than 1.5 A with heavy protein atoms.
   e4) has 10 or more contacts less that 4 A with protein heavy atoms (see 2) and has 1 or more hydrogen bonds with the ligand and 4 or more contacts with polar protein atoms (see 2a).
   e5) has 2 or more contacts with the protein within 3 A and one ligand contact.
   e6) has between 3 or more contacts within 4 A of heavy protein atoms and satisfies these conditions;
   e6a) has less than 10 phobic protein contacts (2) and less than 2 polar protein contacts (2a).
   e6b) if there are 1 polar protein contacts: must have less than 8 phobic protein contacts.
   e6c) has less than 3 heavy atom contacts within 3.5 A.
   e7) has an aromatic hydrogen bond to the ligand defined by: ligand aromatic ring atom (C or N) within 4.7 A of the water and with the angle between the water aromatic ligand atom vector and the 'in plane lone pair' vector of the ligand atom is less than 70 degrees.

e8) water is within 3.7 A of a charged protein atom.

e9) water is within 5 A of a charged protein atom and within 5.5 A of a polar (O N) ligand atom.

if the water satisfies conditions (a-e9) assign a penalty wpen to the water using the following schedule.

If 1 phobic ligand contact and 3 or more phobic protein contacts and a removal fraction less than 0.1 wpen=1.0 kcal/m.

if 2 phobic ligand contacts wpen=2.0 kcal/m.
if 3 phobic ligand contacts wpen=3.0 kcal/m.
if 4 or phobic ligand contacts wpen=4.0 kcal/m.

6) Assign a penalty wpen2 as a function of the total number of phobic-ligand_waterwmap_water contacts 'ilpc=sum_i ilp(i) where ilp(i) is the number of phobic ligand contacts for water i. If water i meets any one of the following criteria 6a-6d then its contribution to the ilpc total in this sum is ignored (i is removed from sum_i).

a) water i has one phobic ligand contact and 2 or more heavy protein atom contacts within 3.5 A.

b) water i does not contact any other waters within 3.5 A that have a removal fraction (3) greater than 70%.

c) water i has a zonzero penalty from step 5.

d) water i is within 4 A of a charged protein atom.

The function for wpen2 with respect to the total phobic ligand contacts ilpc is;

if ilpc=8 wpen2=0.5 kcal/m
if ilpc=9 wpen2=1.0 kcal/m
if ilpc=10 wpen2=1.5 kcal/m
if ilpc=11 wpen2=2.5 kcal/m
if ilpc=12 wpen2=3.5 kcal/m
if ilpc>=13 wpen2=4.0 kcal/m finally the total penalty for phobic water contacts is wpen (step 5)+wpen2 (step 6).

The efficacy of the above invention is demonstrated in the following fashion. Firstly, we have assembled a test suite of 622 protein-ligand complexes of active compounds. As a control for evaluating the method, the examples below involve known crystal structures available in the Research Collaborative for Structural Bioinformatics' publicly accessible Protein Data Bank ("the PDB"). In carrying out optimization, we use poses docked with Glide XP, a scoring function described e.g., in Patent no. US 2007/0061118 A1, filtering the (very small) number of cases for which self-docking yields unsuitable structures. By using docked structures, rather than the crystal structures themselves, in our optimization process, we increase the realism of the model, and also enable it require the use of Glide XP.

The PDB structures can be viewed as a large and diverse training set for the scoring function. Testing of the scoring function under similar conditions can be performed by pharmaceutical the docking to correct small geometrical errors in the crystal structures (e.g. in hydrogen bond distances) which can be crucial to properly assigning scores to these terms. The invention does not require the use of ligands for which crystal structures are known, nor does it require the use of Glide XP.

The PDB structures can be viewed as a large and diverse training set for the scoring function. Testing of the scoring function under similar conditions can be performed by pharmaceutical and biotechnology companies, using proprietary data sets where crystal structures are available. In carrying out these tests, there is no need to release the structures or even to divulge the name of the receptor; one can simply perform the calculations, and report the ability to rank order the compounds as a correlation coefficient.

These complexes give reasonably accurate structures when the ligand is redocked into its native receptor (maximum RMSD is 3.5 A) and their scores, using the most recent version of the Glide XP scoring function, are on average within ~1 kcal/mole of the experimental binding affinity. Thus, the scoring function in the absence of the term constituting the invention works well for complexes of active compounds taken from the PDB.

Figure 2:
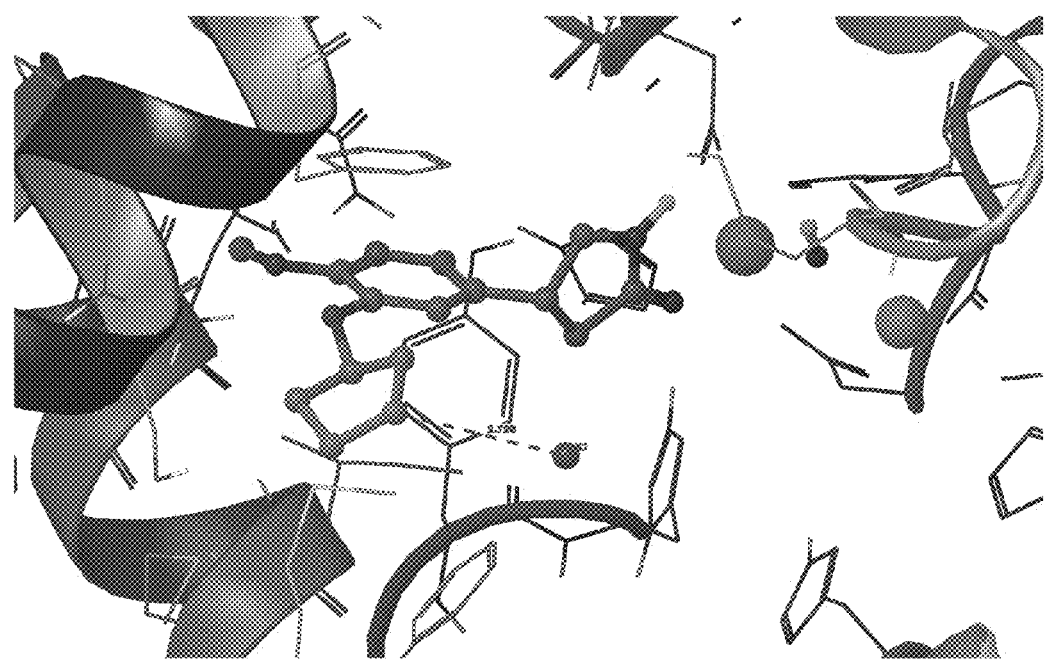
FIG. 2. Active ligand 1r06 is here depicted to be forming unfavorable contacts with water molecule 32. This ligand suffers a computed 2.0 kcal/mol penalty bringing its estimated binding affinity in closer agreement with the experimentally measured value.
Figure 3:
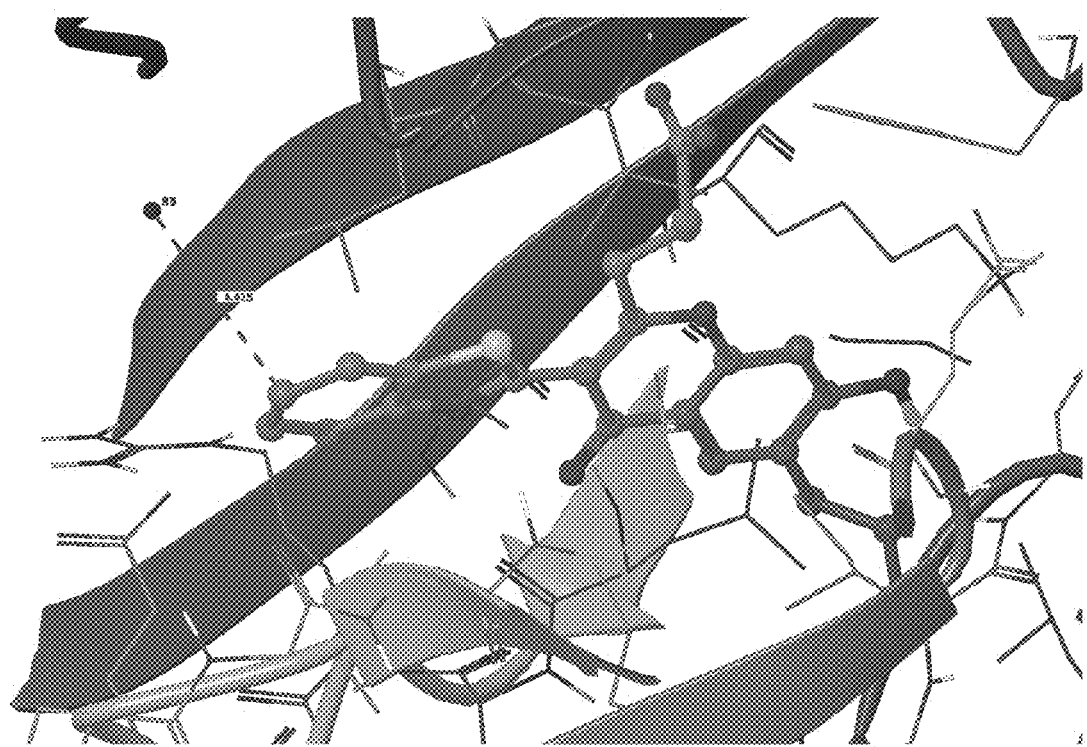
FIG. 3. Decoy ligand 790331 is here depicted to be forming unfavorable contacts with water molecule 53. This ligand suffers a computed 2.0 kcal/mol penalty bringing its estimated binding affinity to −6.5 kcal/mol, which is more consistent with the statistically expected binding affinities of such decoy molecules in a random screen.
Figure 4:
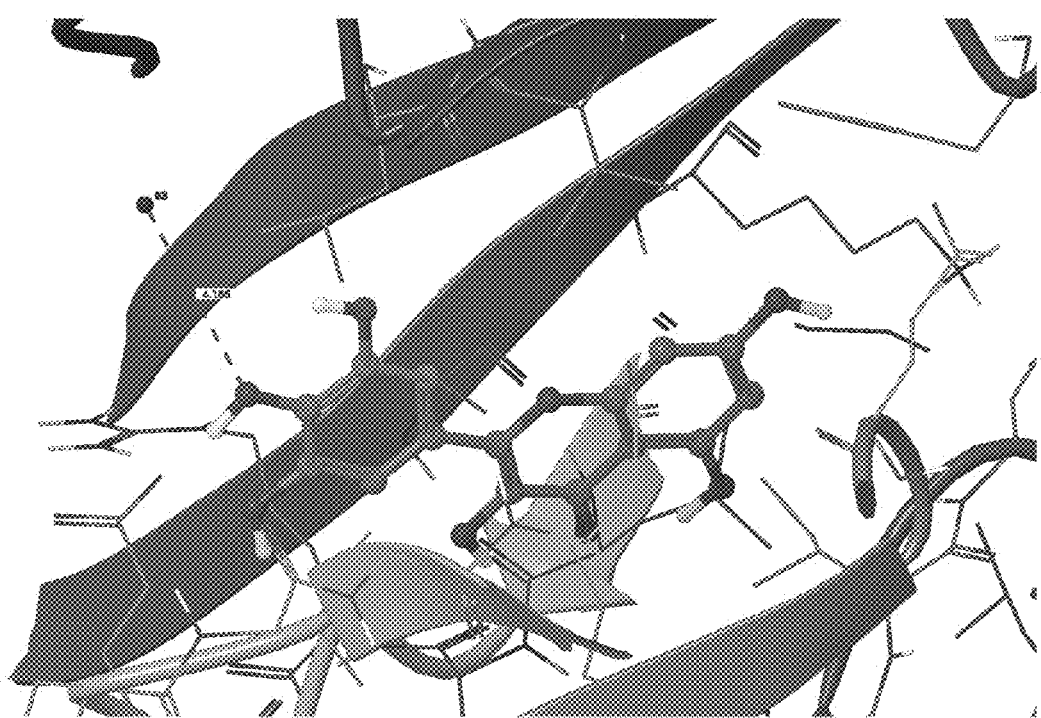
FIG. 4. Active molecule 2o63 depicted here avoids the penalty suffered by decoy 790331 by orienting a hydroxyl group to interact with water molecule 53.

We have added the new term to the Glide XP™ scoring function and rerun the active calculations with it in place. In Table 1, there is a list of PDB complexes which are impacted by this term, the experimental binding affinity of each complex, and the calculated binding affinity with and without the new term. It can be seen that there are very few cases out of the total of 662 complexes where active complexes satisfy the above conditions. In many of these cases, the penalty term improves agreement of the predicted binding affinity of the active complex with experiment. In a small number of cases, agreement becomes worse, but overall the effect of the penalty term averaged over the test cases presented below is favorable (there are 9 favorable cases, and only 3 unfavorable cases). These results demonstrate that the invention as described is not generally a characteristic of complexes of receptors with active complexes, and when it is, it improves agreement of the predicted binding affinity with experiment significantly more frequently than when it makes this agreement worse. Examples of the application of the penalty term are also depicted in FIGS. 1 through 4.

The second criterion for efficacy of the invention is penalizing random database ligands which are assigned highly favorable scores by the current scoring function. In a 1000 compound random database, it is very unlikely that experimentally one would find a compound with a binding affinity that was tighter than 500 nm, or −9 kcal/mole. Therefore a penalty term is improving discriminatory power when it eliminates compounds with binding affinities as good as or better than −9 kcal/mole without inappropriately penalizing any active compounds. Because of the intrinsic fluctuations in the scoring function of 1.5-2 kcal/mole, noted above, we nevertheless expect to see some compounds scoring at the −9.0 kcal/mole level (or a little better); these represent active compounds that experimentally would have binding affinities in the −7.0 to −9.0 range, but which achieve a better score due to the scoring function fluctuations. However, if the experimental hit rate for a 10 micromolar screen is on the order of 0.5% (typical for pharmaceutically interesting targets, although there can be significant deviations in either direction from this value), then one would expect there to be no more than 5 compounds from the random library scoring below −9.0 kcal/mole. Hence, the success in reducing the number of such values for the suite of receptors tested below 5, and in general reducing the number as much as possible, is a good measure of the efficacy of the penalty term.

Table 2 displays the number of ligands from our standard 1000 compound random library of drug like molecules whose scores are less than −9 kcal/mole for several different scoring functions and for 24 test receptors. This specific comparison is meaningful only if the scores for active compounds are close to the experimental scores for these compounds, so in the first column of Table 1 we present results obtained with a version of Glide XP which has been optimized to reproduce the scores of PDB complexes with an average error of ~1 kcal/mole. Penalty terms, such as the current invention, must then be added to this scoring function to improve performance in discriminating active from inactive compounds.

In the second column, we present results obtained when all of our recently developed novel penalty terms, including the present invention, are included in the scoring function. This results in a significant reduction in the number of decoys that score −9 and lower. Finally, to isolate the specific performance of the invention described herein, column three present results of adding the invented term to the scoring function of column 1. The term does not strongly affect every receptor, but there are a significant number of receptors which do demonstrate a measurable, highly relevant improvement. Finally, in column 4, we present results of deleting the invention from the overall best practices scoring function presented in column 3. This data demonstrates that the invention is an important component of the overall best practices method; without it, performance is degraded for a number of receptors.

Taken together, the above data demonstrates unambiguously that the invention described herein make a substantial contribution to discriminating active from inactive compounds in the Glide XP™ empirical scoring function. Similar improvement would be seen in any score function which itself was lacking in a comparable penalty term; to our knowledge, existing published scoring functions do not contain such a term at present. The complete version of the new scoring function, including the invention described here, yields 23/24 receptors with 4 or fewer random database ligands scoring below −9.0. The total number of database ligands scoring below −9.0 that are eliminated by the invention (column 1-column 3), summed over all receptors, is 34, a nontrivial fraction of the total number of ligands achieving this score in the original XP function (column 1).

TABLE 1

Two native pdb ligands affected by the water-phobic contact terms.

| Pdb_system | Score_np | Score_p | dG |
|---|---|---|---|
| Alr2__2dv0 | −12.3 | −11.3 | −11.4 |
| Alr2__2hv5 | −12.1 | −11.1 | −11.4 |
| Alr2__2iq0 | −7.9 | −5.9 | −5.7 |
| Alr2___2isf | −5.2 | −4.7 | −4.7 |
| Chk1__2br1 | −7.6 | −5.6 | −7 |
| Hivrt__1eet | −12.7 | −11.7 | −11.3 |
| Jnk__1pmu | −11.5 | −10.5 | −8.5 |
| Pde4__1y2k | −9.1 | −7.1 | −10.4 |
| Pde4__1ro6 | −11.3 | −9.3 | −8.7 |
| Throm__1g32 | −10.8 | −9.8 | −8.3 |
| Throm__1gj4 | −8.2 | −7.2 | −5.2 |
| Upa__1gjc | −8.7 | −7.2 | −11 | score_np is the unpenalized score and score_p the penalized score, dG is the experimental free energy of binding.

TABLE 2

Number of decoy ligands with scores less than −9 kcal/m for a version of XP without recently developed penalty terms (XP), XP with the newer penalty terms (new XP) and XP with the addition of the water contact term of this patent (XP_wcon) Column 4 has the water contact term removed from newXP (newXP_nowcon).

| Pdb_system | XP_ | newXP | XP_wcon | newXP_nowcon |
|---|---|---|---|---|
| Abl | 24 | 15 | 20 | 18 |
| Alr2 | 18 | 4 | 8 | 4 |
| Jnk | 7 | 2 | 3 | 4 |
| Aur | 2 | 2 | 2 | 2 |
| Cdk2 | 10 | 3 | 8 | 4 |
| Chk1 | 7 | 4 | 5 | 5 |
| Dpp4 | 7 | 1 | 7 | 1 |
| Er | 4 | 0 | 2 | 0 |
| Erk2 | 0 | 0 | 0 | 0 |
| Err | 3 | 2 | 3 | 2 |
| Fviia | 2 | 0 | 0 | 0 |
| Fxa | 0 | 0 | 0 | 0 |
| Hivrt | 11 | 2 | 7 | 8 |
| Hsp90 | 2 | 0 | 1 | 0 |
| Lck | 10 | 3 | 7 | 4 |
| Oppa | 1 | 1 | 1 | 1 |
| Pim1 | 46 | 3 | 46 | 3 |
| Pka | 0 | 0 | 0 | 0 |
| Ppar | 1 | 0 | 0 | 0 |
| Ptp1b | 1 | 1 | 1 | 1 |
| Rho | 5 | 2 | 5 | 2 |
| Throm | 2 | 1 | 2 | 1 |
| Upa | 0 | 0 | 0 | 0 |
| P38 | 0 | 0 | 0 | 0 |

Other embodiments are within the scope of the following claims. Note that the above penalties values are only representative. Typically for physically reasonable ligands the total penalty assessed under this invention will be less than 5 kcal/mole.

APPENDIX I

The hydrophobic atom types are encoded as industry-standard SMARTS patterns. All hydrophobic ligand moieties are those selected with ptype = 1.
The ptype assignment code is order dependent, i.e. a group could match multiple patterns but gets the ptype tothe pattern in the list that is first caught.
Matt

```
# First index is the "ptype"         1: hydrophobic heavy
#                                    2: donor hydrogen
#                                    3: acceptor heteroatom
#                                    4: general polar (non-
#                                       hydrogen bonding)
#                                    5: metal cation
#                                    0: none of the above
# Second index is the hybridization  0: free atom
#                                    1: sp
#                                    2: sp2
#                                    3: sp3
# Third index is the SMARTS pattern for matching
# Fourth index is a descriptive label

# The order of patterns is IMPORTANT - patterns higher in
# the list for a particular element will be preferentially
# matched over a lower pattern.

             #Hydrogens
2    1 [#1][#7]                Hydrogen on nitrogen
2    1 [#1][S;X2]              Hydrogen in thiols
2    1 [#1][O-]                Hydrogen in hydroxide ion
2    1 [#1][O;X2]              Hydrogen in alcohols
0    1 [#1][c,n,o]             Aromatic hydrogen
0    1 [#1][C]                 Hydrogen on carbon
0    1 [#1]                    Default hydrogen
             #Carbons
1    1 C#C                     Alkyne carbon
4    1 C#N                     Nitrile carbon
1    1 [CH2](C#[N-])           Methyl nitrile
4    2 [c](~[n])~[n]           Aromatic amidine
1    2 [c]                     Aromatic carbon
1    2 C=C                     Alkene carbon
4    3 [CX4](~[O,N,n])~[O,N,n] Tetrahedral carbon to two
                                  N/O attachments
1    2 [CX3](=[N])([NX3])[NX3] Guanidine carbon
4    2 C(=O)[O]                Carbonyl carbon - acid
4    2 C(=[O,S])[N;X3]         Carbonyl carbon - amine/
                                  thioamine
4    2 C=[O,N,S]               Default carbonyl carbon
1    1 [C;X2]                  Default sp carbon
1    2 [C;X3]                  Default sp2 carbon
1    3 [C;X4]                  Default sp3 carbon
```

APPENDIX I-continued

The hydrophobic atom types are encoded as industry-standard SMARTS patterns. All hydrophobic ligand moieties are those selected with ptype = 1.
The ptype assignment code is order dependent, i.e. a group could match multiple patterns but gets the ptype tothe pattern in the list that is first caught.
Matt

| | | |
|---|---|---|
| 1 | 3 [#6] | Default carbon |
| #Nitrogens | | |
| 3 | 1 [N]#C | Nitrogen in nitrile |
| 4 | 2 [n;X3] | Aromatic nitrogen with three neighbors |
| 3 | 2 [n] | Aromatic nitrogen |
| 3 | 2 N(=N=N) | Azide nitrogen |
| 3 | 2 N(=N)=N | Azide nitrogen central atom |
| 3 | 2 [N;X2]=C[N;X3] | Neutral amidine nitrogen |
| 4 | 2 [N;X3][*]=[*] | Conjugated nitrogen |
| 4 | 2 [N;X3][c,n]~[c,n,o] | Aromatically conjugated nitrogen |
| 4 | 2 [NX3;+] | Nitrogen |
| 3 | 2 [NX2] | Imine nitrogen |
| 4 | 3 [NH3] | Ammonia nitrogen |
| 4 | 3 [NX4;+] | Protonated nitrogen |
| 3 | 1 [N;X1] | Default sp nitrogen |
| 3 | 2 [N;X2] | Default sp2 nitrogen |
| 3 | 3[N;X3] | Default sp3 nitrogen |
| 3 | 3 [#7] | Default nitrogen |
| #Oxygens | | |
| 3 | 2 [O;X1]~[N;X3]~[O;X1] | Nitro oxygen atoms |
| 3 | 2 [O;X1;-]C=[O;X1] | Carboxylic acid oxygen |
| 3 | 2 [O-][P,S] | Phosphate/sulphone oxygen |
| 3 | 3 [O-] | Oxygen anion |
| 3 | 3 [o] | Aromatic oxygen |
| 3 | 2 [O;X1] | Oxygen sp2 default |
| 3 | 3 [O;X2] | Oxygen sp3 default |
| 3 | 2 [#8] | Default oxygen |
| #2nd row elements | | |
| 4 | 3 [#15] | Default phosphorous |
| 1 | 2 [s] | Aromatic sulfur |
| 4 | 2 [SX1]=[*] | Thiocarbonyl sulfur |
| 3 | 3 [S-;X1] | Thiolate anion sulfur |
| 4 | 3 [SX2;H1] | Thiol sulfur |
| 1 | 2 [SX2] | Disubstituted sulfur |
| 4 | 3 S(=O)(=O)([C,N])([C,N]) | Sulfur in sulfone/sulfonamide |
| 4 | 3 S(=O)([#6])([#6]) | Sulfur in sulfoxide |
| 4 | 3 [SX4] | Default sulfur |
| 4 | 3 [#16] | Default sulfur |
| #Halogens | | |
| 3 | 0 [F-] | Flourine ion |
| 3 | 0 [Cl-] | Chlorine ion |
| 4 | 0 [Br-] | Bromine ion |
| 4 | 0 [I-] | Iodine ion |
| 4 | 1 [#9] | Default fluorine |
| 1 | 1 [#17] | Default chlorine |
| 1 | 1 [#35] | Default bromine |
| 1 | 1 [#53] | Default iodine |
| #Ions | | |
| 5 | 0 [*;X0] | Free metal ion |

What is claimed is:

1. A method of scoring binding affinity of a proposed ligand molecule for a receptor molecule using a sufficiently programmed computer for the following steps:
  a. obtaining computer stored data representing a predicted ligand-receptor structure,
  b. determining whether the receptor alone, without a docked ligand, includes one or more hydration sites occupied by localized water, and, if so,
  c. determining if after docking a receptor-localized water interacts with a hydrophobic ligand atom, and if the docking of the ligand into the receptor results in unfavorable interaction of the ligand with a localized water molecule occupying a receptor hydration site,
  d. determining whether one or more of the exceptions conditions i.-iv. is present:
    i. the hydrophobic ligand atom has a net positively charged ligand atom positioned a distance of 4 atoms or fewer from the hydrophobic ligand atom, where the distance is determined by bond connectivity of the atoms in the ligand;
    ii. the hydrophobic ligand atom that is part of a ligand —CH3 group, or a ligand atom within 3 atoms of a —CH3 group, where the localized water borders the edge of a hydrophobic pocket giving it access to surrounding water;
    iii. the localized receptor water is positioned within 5 Å of a positively charged ligand atom;
    iv. the localized receptor water has hydrogen bonds to the ligand;
  e. applying a penalty to scoring function of binding affinity if 1) the localized receptor water interacts with a hydrophobic ligand atom as determined in step c, and 2) none of the exception conditions i. iv. is present.

2. The method of claim 1 in which the localized receptor hydration sites are determined by computerized sampling of receptor sites for hydration followed by computerized assignment of water occupancies for the various sampled sites.

3. The method of claim 1 comprising using a computer programmed to assess a penalty only if localized water within a hydration site interacts with a hydrophobic ligand atom at a distance of 5 Å or less.

4. The method of claim 3 comprising using a computer programmed to determine whether exception condition b. i is present and not assessing the penalty if condition b.i. is present.

5. The method of claim 3 in which Cl, Br or both are not considered hydrophobic ligand atoms.

6. The method of claim 3 comprising using a computer programmed to determine whether exception condition b. ii. is present and not assessing the penalty if condition b.ii. is present.

7. The method of claim 1 comprising using a computer programmed to determine whether exception condition b. iii. is present and not assessing the penalty if condition b.iii. is present.

8. The method of claim 1 comprising using a computer programmed to determine whether exception condition b. iv. is present and not assessing the penalty if condition b.iv. is present.

9. The method of claim 1 in which receptor sites with a localized water are determined to be waters that are predicted to have an occupancy in the reference frame of the protein of >1.5× the bulk water occupancy.

10. The method of claim 2 in which molecular dynamics simulations are used to determine water occupancy.

11. The method of claim 10 in which an active-site solvation analysis is used to identify localized water sites.

12. The method of claim 1 in which a penalty is applied to the binding affinity score of the ligand when the free energy of displacement of a water molecule from the receptor site into bulk waters is determined to be more favorable than a specified cutoff value.

13. The method of claim 1 in which a penalty is applied to the binding affinity score of the ligand by a method comprising estimating the energetic favorability of the water molecule in the hydration site from the hydrophobicity of the site or from specific interactions with receptor groups.

14. The method of claim 13 in which estimating the energetic favorability of the hydration site includes calculation selected from the group consisting of molecular dynamics simulations, Monte Carlo simulations, exhaustive enumeration of geometries of the water molecule within the site, and optimization (via for example energy minimization) of the position of the water molecule within the site.

15. The method of claim 12 in which the cutoff value is at least 0 kcal/mole.

16. The method of claim 12 in which free energies of displacement of a water molecule from the receptor site into bulk water is determined by molecular dynamics simulation followed by the application of modified inhomogeneous solvation theory to assign displacement free energies.

* * * * *

UNITED STATES PATENT AND TRADEMARK OFFICE
CERTIFICATE OF CORRECTION

PATENT NO. : 8,510,058 B2
APPLICATION NO. : 13/079725
DATED : August 13, 2013
INVENTOR(S) : Richard A. Friesner et al.

Page 1 of 1

It is certified that error appears in the above-identified patent and that said Letters Patent is hereby corrected as shown below:

In the Claims

Column 14, line 23, claim 1, delete "i.iv." and insert -- i.-iv. --

Signed and Sealed this
Fifth Day of November, 2013

Teresa Stanek Rea
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,510,058 B2 | |
| APPLICATION NO. | : 13/079725 | |
| DATED | : August 13, 2013 | |
| INVENTOR(S) | : Richard A. Friesner and Robert Murphy | |

It is certified that error appears in the above-identified patent and that said Letters Patent is hereby corrected as shown below:

In the Claims

Col. 14, line 11, in Claim 1, delete "that is part" and insert -- is not part --

Signed and Sealed this
Thirtieth Day of June, 2015

Michelle K. Lee
*Director of the United States Patent and Trademark Office*